United States Patent [19]
Burns

[11] Patent Number: 5,458,113
[45] Date of Patent: Oct. 17, 1995

[54] COLLECTION ASSEMBLY

[75] Inventor: James A. Burns, Elizabeth, N.J.

[73] Assignee: Becton Dickinson and Company, Franklin Lakes, N.J.

[21] Appl. No.: 289,721

[22] Filed: Aug. 12, 1994

[51] Int. Cl.⁶ ................................................. A61B 5/00
[52] U.S. Cl. ........................... 128/763; 215/343; 422/102
[58] Field of Search ........................... 128/760, 763–766; 604/317, 403; 422/102; 215/343–346, 354, 355

[56] References Cited

U.S. PATENT DOCUMENTS

| | | | |
|---|---|---|---|
| 3,281,000 | 10/1966 | Lowen | 215/344 |
| 4,238,042 | 12/1980 | Hatakeyama et al. | 215/343 |
| 4,844,273 | 7/1989 | Hawkins | 215/343 |
| 5,257,984 | 11/1993 | Kelly | 128/763 |
| 5,275,287 | 1/1994 | Thompson | 215/343 |

FOREIGN PATENT DOCUMENTS

0494847  7/1992  European Pat. Off. ............... 128/764

*Primary Examiner*—Max Hindenburg
*Attorney, Agent, or Firm*—Alan W. Fiedler

[57] ABSTRACT

The present invention is a collection assembly useful for collecting small quantities of blood. The assembly comprises a container with an integral lip for facilitating collection of the blood and a cap suitable for enclosing the container. The assembly further comprises a sealing arrangement for securing the cap to the container using a protrusion on the cap and a thread on the container, wherein the protrusions on the cap travel on the thread to facilitate securing and unsecuring the cap on the container, when the cap is rotated on the container.

5 Claims, 7 Drawing Sheets

COLLECTION ASSEMBLY

BACKGROUND OF THE INVENTION

1. Field of the Invention

The present invention relates to a collection assembly and, more particularly, to a microcollection container and cap suitable for collecting small quantities of blood from a patient and maintaining the blood in secure fashion for subsequent testing.

2. Description of Related Art

Analytical instrumentation has made it possible to carry out a variety of hematological diagnostic procedures on very small quantities of blood. Because of this, a patient's finger or earlobe, for example, may be punctured and a very small quantity of blood may be rapidly collected into a container for such testing. However, in order to carry out testing and analysis on small quantities of blood, the blood must be rapidly collected prior to any coagulation thereof.

A collection arrangement as described in U.S. Pat. No. 5,288,466, has been provided wherein a cap having a sealing element is configured to fit the top of a microcollection container having a lip for engaging the puncture site and transferring blood to the container. However, with such an arrangement, when a sample is taken, blood droplets may be left in and around the top area of the container or on the bottom of the sealing element. Therefore, excess blood may be aspirated when the cap is attached to and removed from the top of the container.

SUMMARY OF THE INVENTION

The present invention is a collection assembly comprising a container and a cap. The cap preferably comprises a closed top portion, an open bottom portion, and an annular skirt having an inner surface and an outer surface. The cap further includes an inner skirt portion generated from the closed top portion that does not extend as long as the annular skirt and is closed off at its extremity by a sealing ring. The sealing ring protrudes into an annular space between the two skirts. The cap further comprises a bottom stop ledge at the open end of the annular skirt and a shield that extends from the outer surface of the annular skirt.

The container preferably comprises an open top portion, a closed bottom portion, a sidewall extending from the top portion to the bottom portion and an open end associated with the top portion having an integral collector or lip portion. Most preferably the integral collector is a scoop that is the same diameter as the inner diameter of the container so that no air vent is required.

The container further includes a cap seating flange associated with the outer diameter of the top portion of the container, an extending annular skirt associated with the bottom portion and a blood trap or trough positioned within the cap seating flange.

Preferably, the collection assembly includes means for securing the cap to the top portion of the container by the interaction of protrusions on the cap with threads on the container and the sealing ring of the cap with the inside surface of the top portion of the container. Alternatively, the collection assembly includes means for securing the cap to the container with the protrusions on the container and threads on the cap. These arrangements assist in substantially reducing fluid splatter from the container.

Another advantage of the present invention is that any excess fluid on the outside surface of the integral collector will flow into the blood trap or trough of the cap seating flange as the cap and container are being secured. Therefore, radial spray of excess fluid is minimized and any excess fluid on the top of the cap seating flange will be directed downward between the outer diameter of the cap seating flange and the cap shield.

Still another advantage of the invention is that only the sealing-ting makes contact with fluid collected in the container. Therefore the inner surfaces of the cap may be minimally exposed to fluid collected in the container when the cap is secured to the top portion of the container and again radial spray of excess fluid is minimized during cap removal.

Another advantage of the present invention is that, when the cap is secured to the container, the flange on the container is not covered completely by the shield on the cap, so that when the capped assembly is centrifuged the load is on the flange and the cap is not loosened.

DETAILED DESCRIPTION

Figure 1:
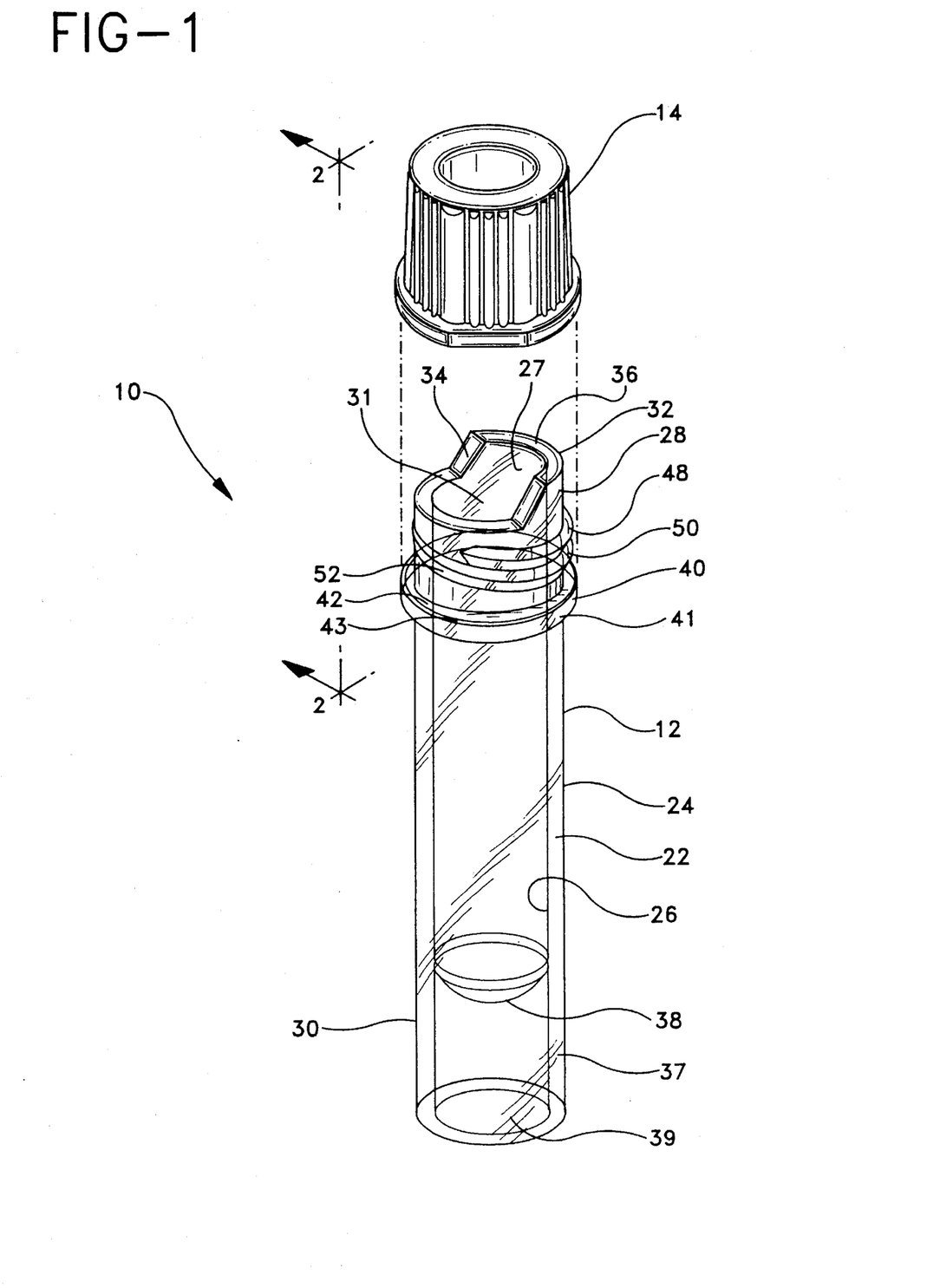
FIG. 1 is a perspective view of the preferred collection assembly illustrating the container with the cap unsecured.

Referring to the drawings in which like reference characters refer to like parts throughout the several views thereof, FIG. 1 is a perspective view of a preferred collection assembly 10 illustrating a container 12 with a cap 14 unsecured.

As illustrated in FIG. 1, container 12 has a sidewall 22 having an outer surface 24 and an inner surface 26. Sidewall 22 extends from an upper portion 28 to a lower portion 30. Upper portion 28 includes an open end 31 and an inner surface 27 with a top surface 32 having an integral lip portion 34 with a receiving edge 36. Lower portion 30 comprises a closed bottom end 38 and an annular skirt 37 extending from closed bottom end 38 to define a compartment area 39. Annular skirt 37 provides means for allowing container 12 to be placed upright on a flat surface and means for receiving cap 14 in compartment area 39.

Upper portion 28 has a cap seating flange 40 positioned around outer surface 24 of container 12 which defines a well or trough 42 having an outer wall 41 with an upper surface edge 43. Further positioned on upper portion 28 of container 12 is a single continuous thread 48 that is positioned between receiving edge 36 of integral lip portion 34 and cap seating flange 40. Thread 48 has an upper edge 50 and a lower edge 52 that aid in guiding cap 14 down onto upper portion 28.

Figure 2:
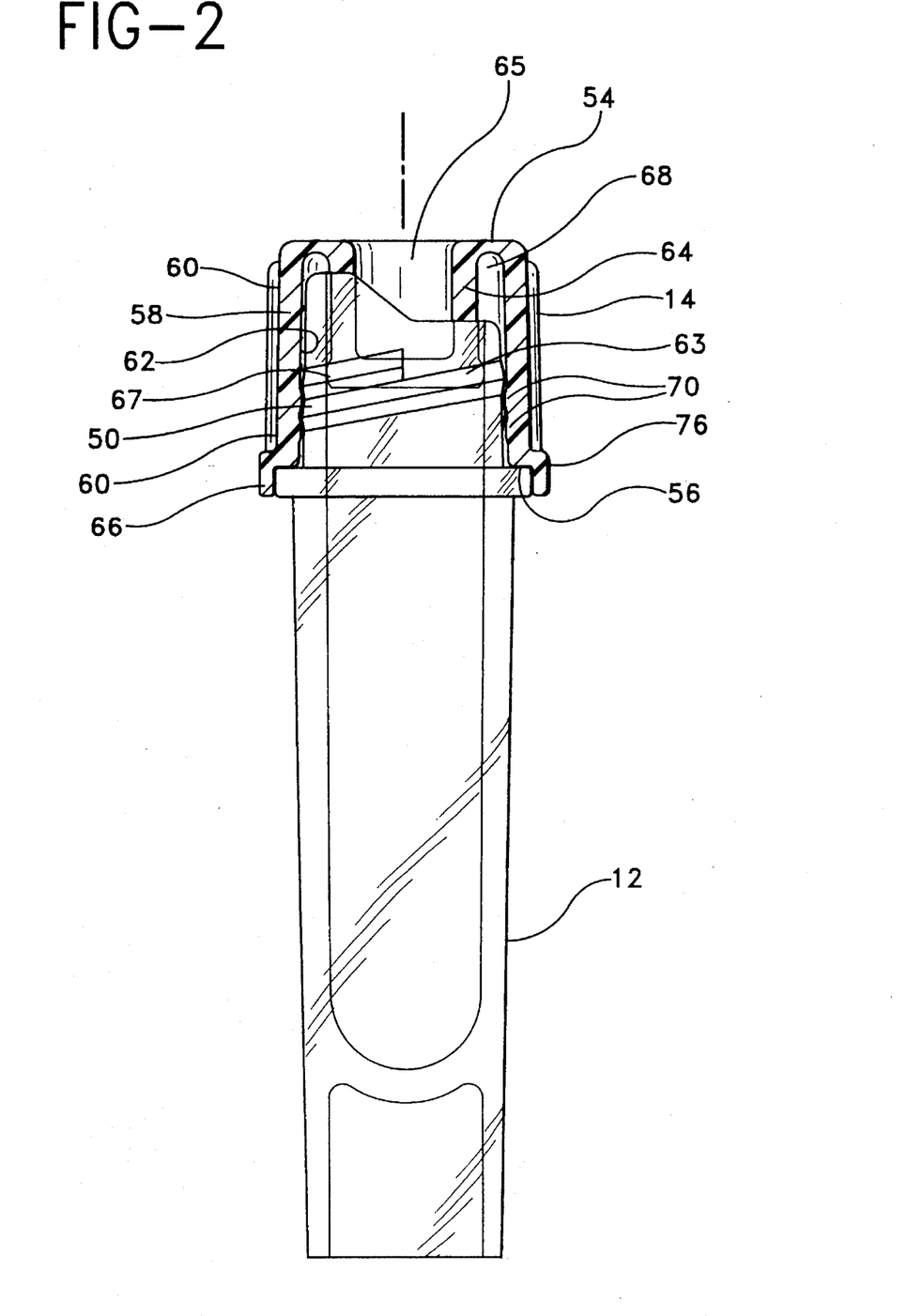
FIG. 2 is a cross-sectional view of the container of FIG. 1 with the cap secured thereto.

FIG. 2 is a cross-sectional view of container 12 with cap 14 secured thereto, FIG. 2 shows the interaction between container 12 and cap 14. Cap 14 includes a top surface 54, a bottom stop ledge 56 and an annular outer skirt 58 extending from top surface 54 to bottom stop ledge 56. Annular outer skirt 58 has an outer wall surface 60 and an inner wall surface 62, and a shield 66 extending from the bottom of outer wall surface 60 of annular outer skirt 58 having an outer surface or circumference 76.

As shown in FIG. 2, cap 14 also includes an inner annular recessed skirt 64 that extends from top portion 54 to a bottom surface 63. Recessed skirt 64 defines a compartment or cup area 65 in top surface 54 of cap 14. Inner wall surface 62 of annular outer skirt 58 and inner annular recessed skirt 64 are spaced from each other to define an annular space 68. Cap 14 further includes a plurality of protrusions 70 positioned on inner wall surface 62 and a sealing ring 67 positioned on recessed skirt 64.

Figure 3:
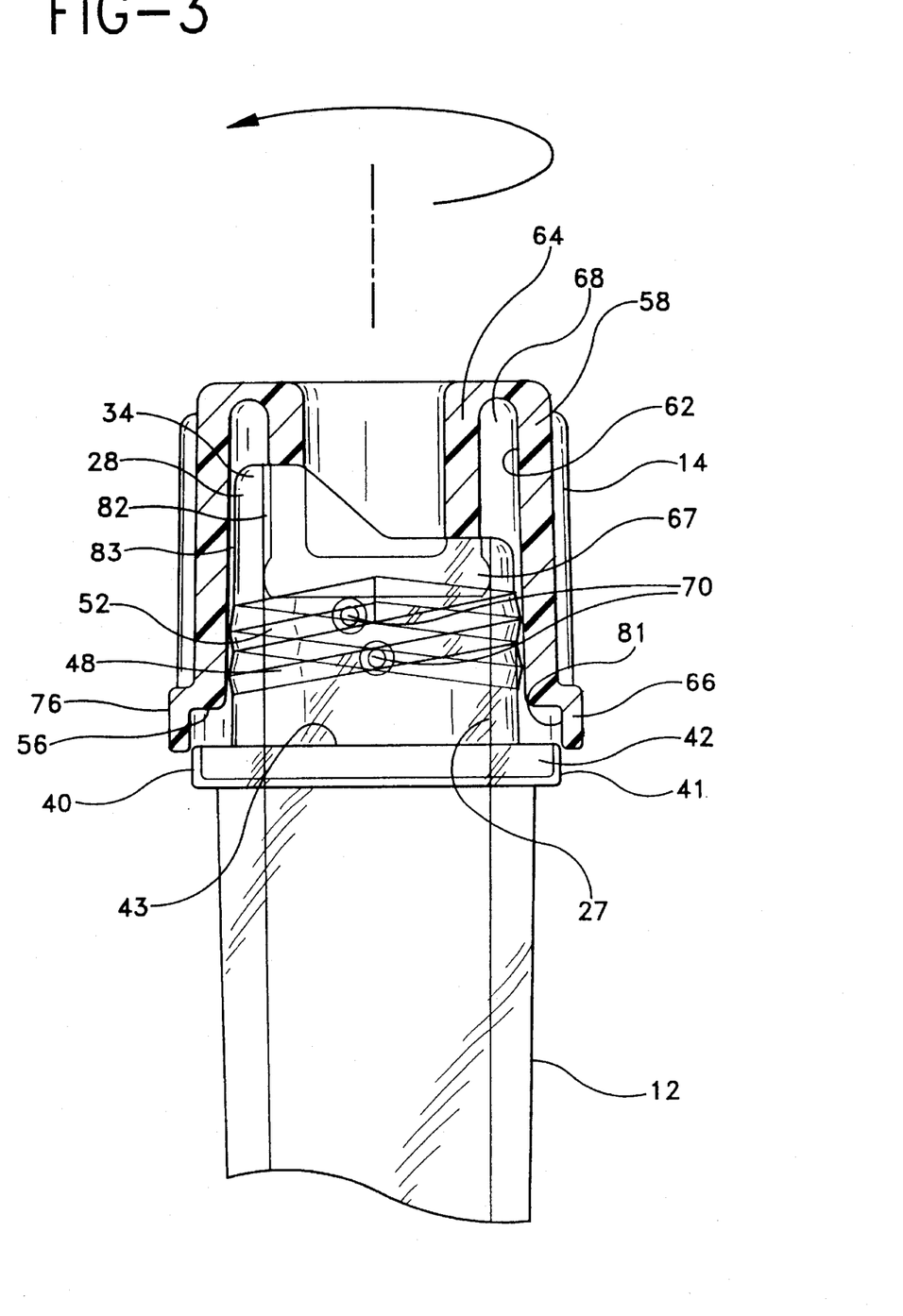
FIG. 3 is an enlarged cross-sectional view of the container and cap of FIG. 1, with the cap in an unlocked position.

As shown in FIG. 3, when cap 14 is in the unlocked position on container 12, space 68 of cap 14 receives upper portion 28 of container 12 including integral lip portion 34, protrusions 70 bear against lower edge 52 of thread 48 of container 12 and sealing ring 67 bears against inner surface 27 of container 12. Shield 66 begins to cover outer wall 41 of cap seating flange 40 until bottom stop ledge 56 finally abuts with upper surface edge 43 of cap seating flange 40, as shown in FIG. 2, so as to form a non-permanent lock and substantially prevent any excess fluid in well 42 of cap seating flange 40 from spilling out. Any fluid that migrates between upper surface edge 43 and bottom stop ledge 56 is directed in a downward direction along container 12 by an inner surface 81 of shield 66 to minimize radial spray. In addition, spaces 82 and 83 remain between integral lip portion 34 and skirts 58 and 64, respectively, to prevent blood on lip portion 34 from being (i) wiped upward or splattered when cap 14 is removed from container 12 and (ii) pushed down towards bottom stop ledge 56 when cap 14 is secured to container 12. Further, any fluid in well 42 is substantially contained by upper surface edge 43 of cap seating flange 40 and bottom stop ledge 56 of cap 14. Outer surface 76 of shield 66 does not cover cap seating flange 40 of container 12 completely when fully seated, as shown in FIG. 2, so that when the capped assembly is centrifuged the load is on flange 40 and cap 14 is not loosened.

Figure 4:
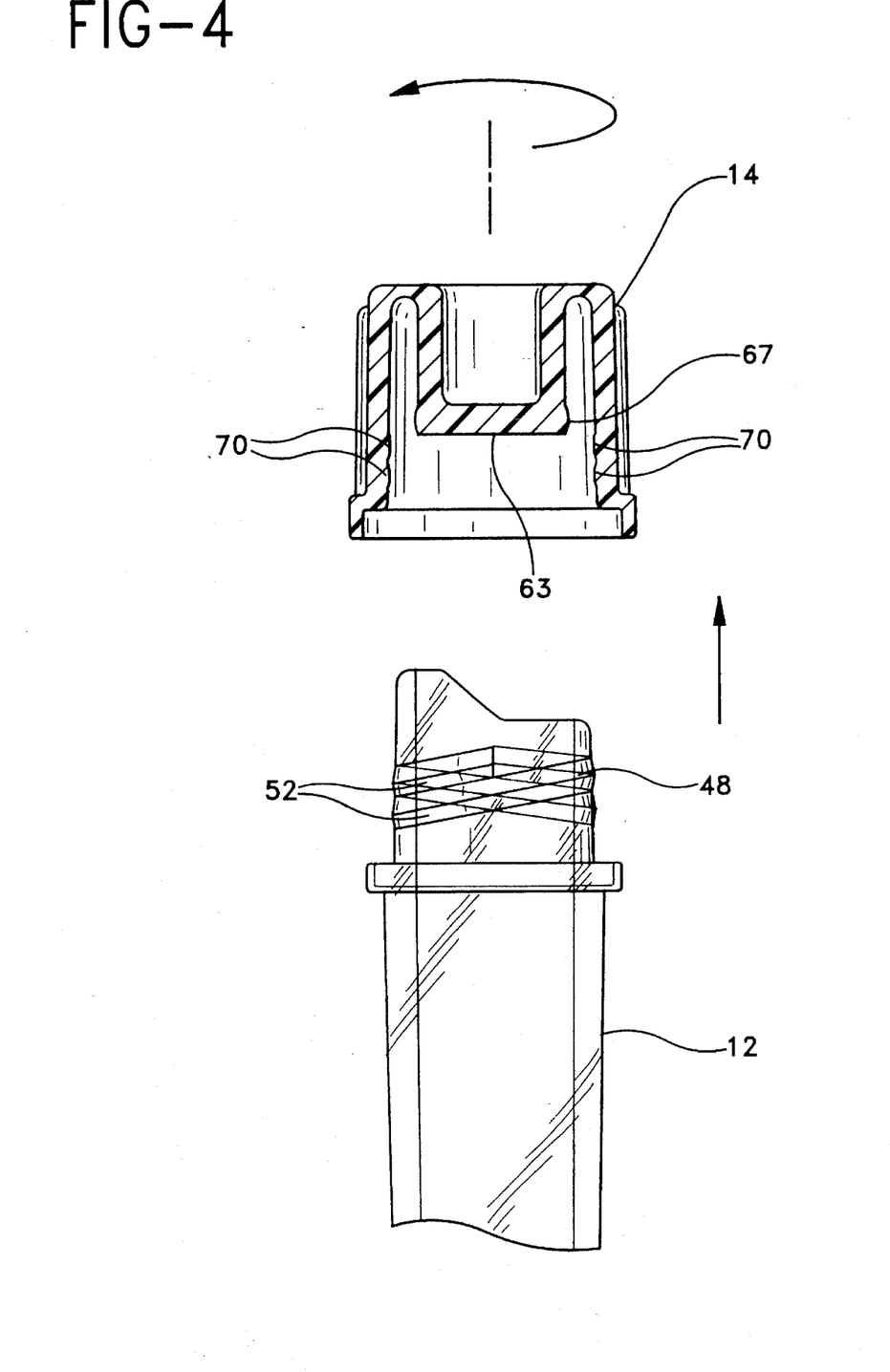
FIG. 4 is an elevational and partial cross-sectional view of the container and cap of FIG. 1, with the cap removed.
Figure 5:
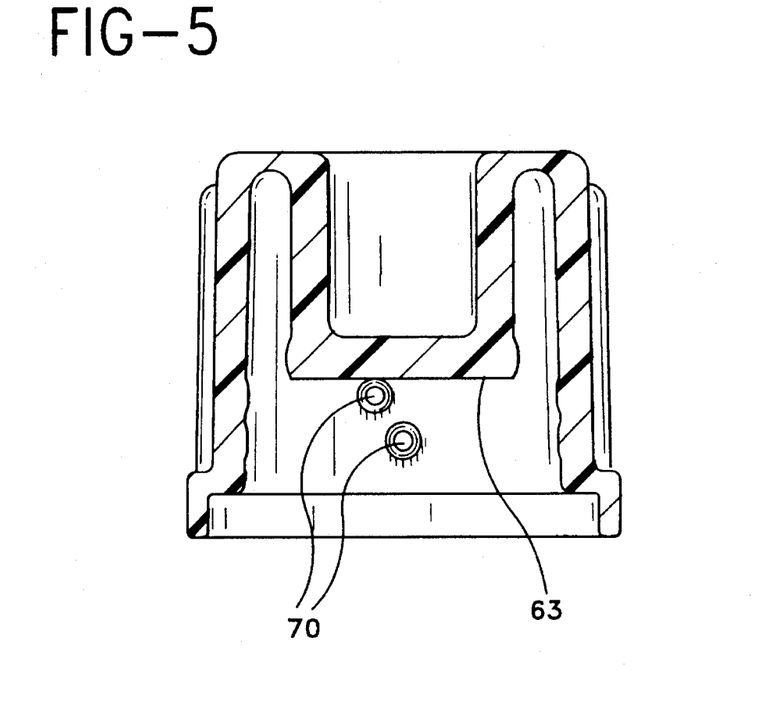
FIG. 5 is an enlarged cross-sectional view of the cap shown in FIGS. 1–4.
Figure 6:
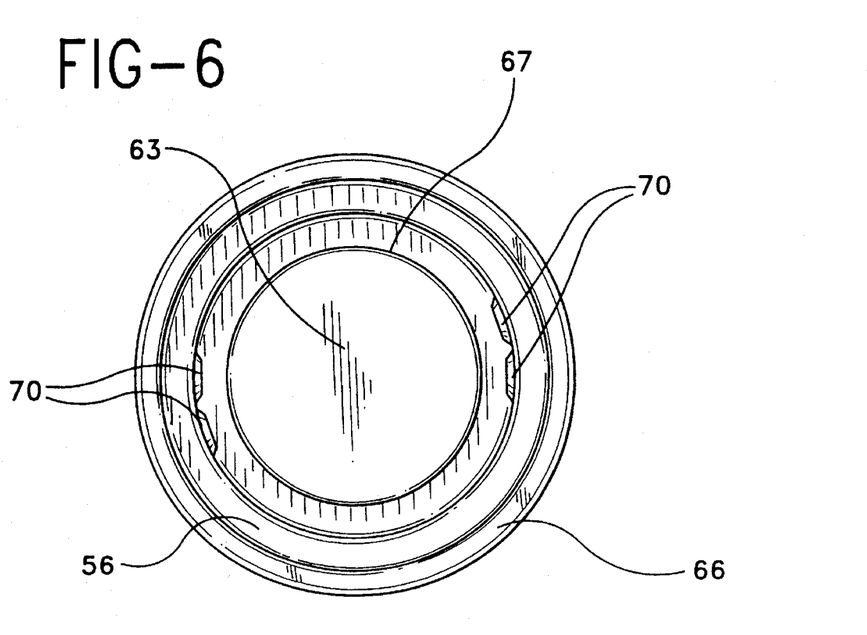
FIG. 6 is a bottom elevational view of the cap of FIG. 5.

As more clearly shown in FIG. 4, cap 14 is rotatably attached to upper portion 28 of container 12 using threads 48 on container 12 and protrusions 70 within cap 14 with protrusions 70 bearing against lower edge 52 of threads 48. FIGS. 5 and 6 show a cross-sectional view and a bottom elevational view, respectively, of cap 14 and more clearly show the location of protrusions 70 within cap 14. Cap 14 can also be snapped over threads 48 and then turned clockwise slightly for final seating and locking on cap seating flange 40 without blood splatter. Likewise, cap 14 can then be turned counter-clockwise for unlocking and removal from container 12 without causing blood splatter.

Figure 7:
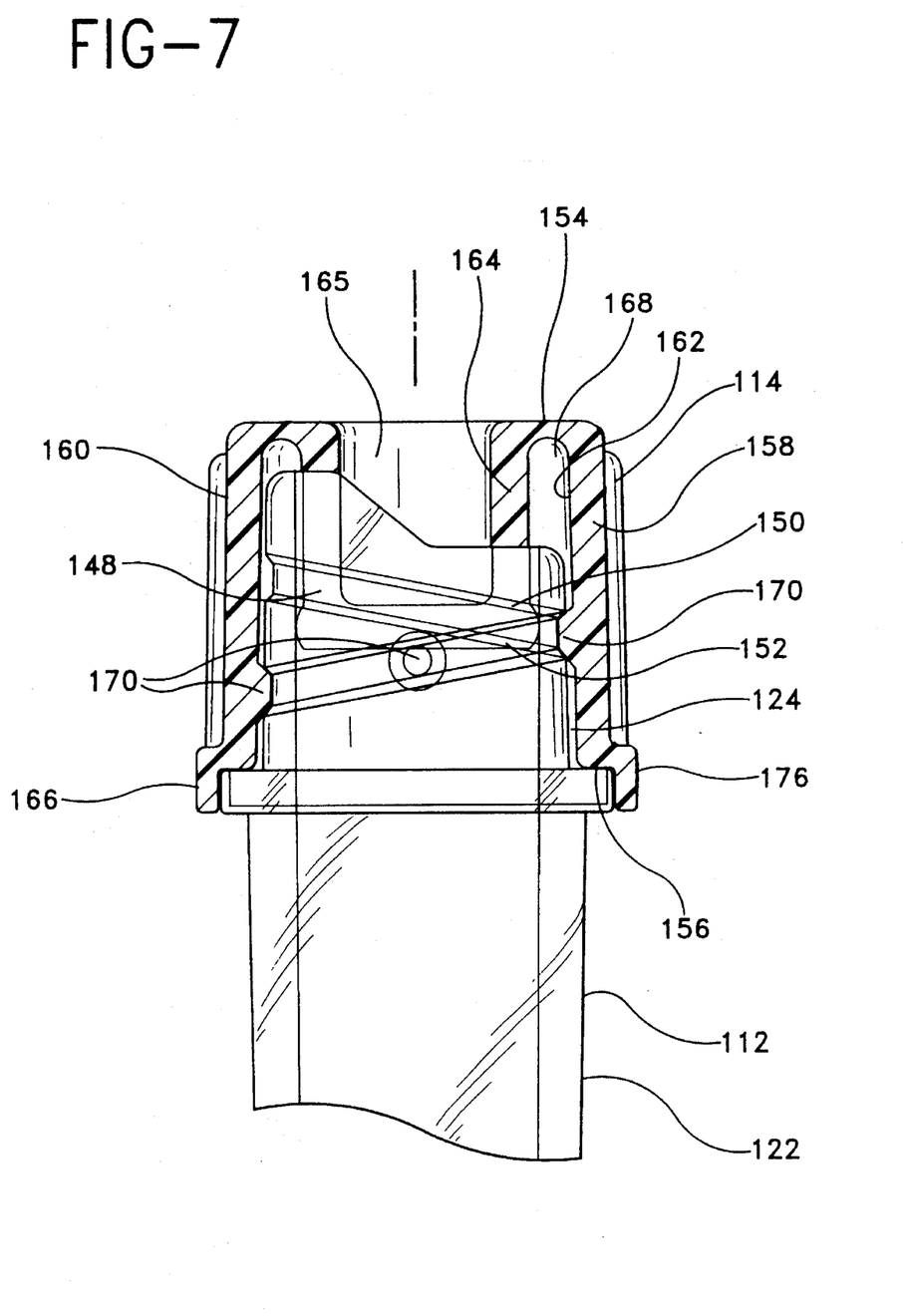
FIG. 7 is a cross-sectional view of an alternative container and cap according to the present invention, with the cap secured to the container.
Figure 8:
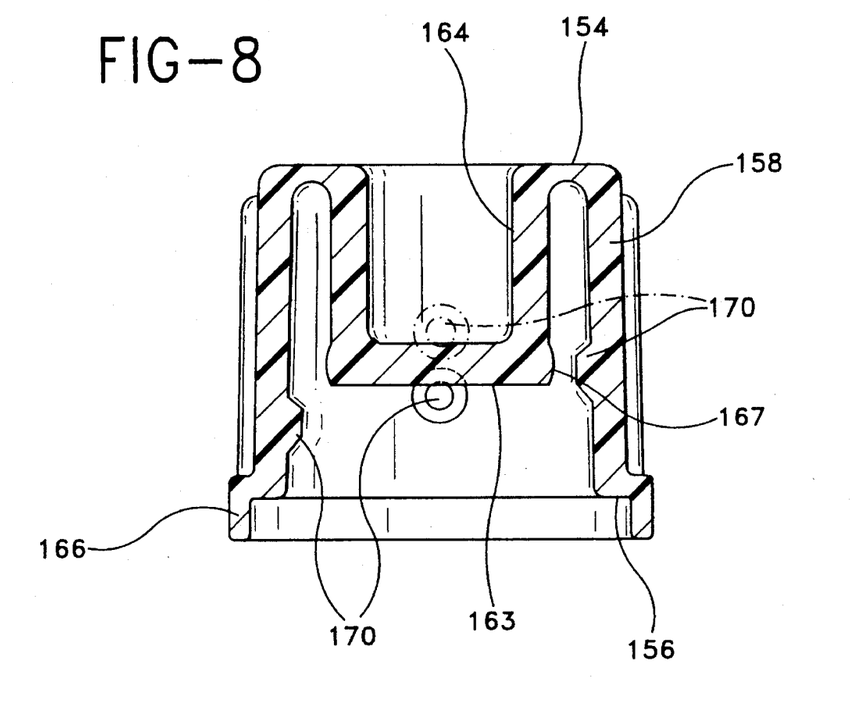
FIG. 8 is an enlarged cross-sectional view of the cap shown in FIG. 7.
Figure 9:
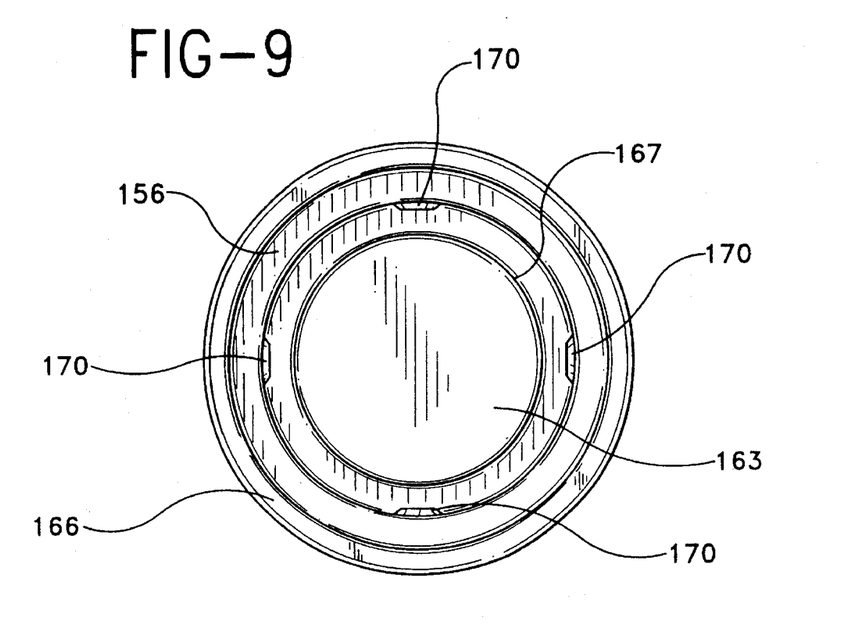
FIG. 9 is a bottom elevational view of the cap shown in FIG. 8.

FIGS. 7–9 show an alternative a container 112 and a cap 114 assembly according to the present invention. FIG. 7 is a cross-sectional view of the assembly cap 114 secured to container 112. FIG. 8 is an enlarged cross-sectional view of cap 114 and FIG. 9 is a bottom elevational view of cap 114. Container 112 is very similar to container 12, discussed above, but includes a thread 148 that is a groove in outer surface 124 of a sidewall 122. Thread 48 on container 12, however, is a protrusion extending from outer surface 24. The other features of container 112 are the same as those in container 12, discussed above. Thread 148 includes an upper edge 150 and a lower edge 152 that aid in guiding cap 114 down onto upper portion 128.

As shown in FIGS. 7–9, cap 114 includes a top surface 154, a bottom stop ledge 156 and an annular outer skirt 158 extending from top surface 154 to bottom stop ledge 156. Annular outer skirt 158 has an outer wall surface 160 and an inner wall surface 162, and a shield 166 extending from the bottom of outer wall surface 160 of annular outer skirt 158 having an outer surface or circumference 176.

Cap 114 also includes an inner annular recessed skirt 164 that extends from top portion 154 to a bottom surface 163. Recessed skirt 164 defines a compartment or cup area 165 in top surface 154 of cap 114. Inner wall surface 162 of annular outer skirt 158 and inner annular recessed skirt 164 are spaced from each other to define an annular space 168. Cap 114 further includes a plurality of protrusions 170 positioned on inner wall surface 162 and a sealing ring 167 positioned on recessed skirt 164. Protrusions 170 are dimensioned and located on inner wall surface 162 to travel within thread 148 on container 112 and aid in securing and unsecuring cap 114 in a smooth manner to prevent spraying during such operations. Exemplary cap 114 shows four protrusions 170, of course, more or fewer could be used and still fall within the scope of the present invention.

The collection assembly of the invention may be made of a molded thermoplastic material so that the specimen collected may be readily viewed. Representative materials include, for example, polyethylene, polypropylene and polyvinyl chloride. The collection container may incorporate a hydrophilic material or a silicon, or a texture may be applied to the internal surface thereof for enhancing the flow and mixing of blood introduced into the container.

Although it is within the purview of the invention to provide caps which are colored to define specific forms of fluid collection containers containing materials for one reason or another or for defining the kind of examination to be conducted on the specimen collected, transparent caps may be provided. Also, it should be noted that the dimensions of the container are such as to provide space for labeling which may be important for identifying the collected specimens.

What is claimed is:

1. A collection assembly comprising:

a cap comprising a closed top portion and an open bottom portion; said cap further comprising:

an outer skirt extending from said closed top portion to said open bottom portion and having an inner surface;

a closed bottom inner skirt surrounded by said outer skirt and extending from said closed top portion toward said open bottom portion; and a protrusion extending from said inner surface of said outer skirt; and a container comprising an open top portion, a closed bottom portion and a side wall having an outer surface; said container further comprising:

an integral lip extending from said open top portion;

a cap seating flange on said outer surface of said container positioned where said integral lip extends from said top portion;

a trough within said cap seating flange; and securing means on said outer surface of said container positioned between said integral lip and said cap seating flange, said securing means interacting with said protrusion on said cap to secure said cap to said container and facilitate removal of said cap from said container upon rotation of said cap, said securing means comprising a groove in said outer surface of said container for receiving said protrusion on said cap.

2. The assembly of claim 1, wherein said closed bottom inner skirt defines a cup shaped compartment in said closed top portion.

3. A collection assembly comprising:

a cap comprising a closed top portion and an open bottom portion; said cap further comprising:

an outer skirt extending from said closed top portion to said open bottom portion and having an inner surface;

a closed bottom inner skirt surrounded by said outer skirt and extending from said closed top portion toward said open bottom portion; and a protrusion extending from said inner surface of said outer skirt; and a container comprising an open top portion, a closed bottom portion and a side wall having an outer surface; said container further comprising;

an integral lip extending from said open top portion;

a cap seating flange on said outer surface of said container positioned where said integral lip extends from said top portion, a trough within said cap seating flange; and securing means on said outer surface of said container positioned between said integral lip and said cap seating flange, and securing means interacting with said protrusion on said cap to secure said cap to said container and facilitate removal of said cap from said container upon rotation of said cap, said securing means comprising a protrusion extending from said outer surface of said container and around the circumference of said container to receive and mate with said protrusion on said cap.

4. The assembly of claim 3, wherein said closed bottom inner skirt defines a cup shaped compartment in said closed top portion.

5. A collection assembly comprising:

a cap comprising a closed top portion and an open bottom portion; said cap further comprising:

an outer skirt extending from said closed top portion to said open bottom portion and having an inner surface;

a closed bottom inner skirt surrounded by said outer skirt and extending from said closed top portion toward said open bottom portion and having a cup shaped compartment therein; and a plurality of protrusions extending from said inner surface of said outer skirt; and a container comprising an open top portion, a closed bottom portion and a side wall having an outer surface; said container further comprising:

an integral lip extending from said open top portion;

a cap seating flange on said outer surface of said container positioned where said integral lip extends from said top portion;

a trough within said cap seating flange; and securing means on said outer surface of said container positioned between said integral lip and said cap seating flange, said securing means comprising a single continuous thread extending from said outer surface and around the circumference of said container to receive and interact with said protrusions on said cap to secure said cap to said container and facilitate removal of said cap from said container upon rotation of said cap.

* * * * *